United States Patent
Kumar et al.

(10) Patent No.: US 12,244,999 B2
(45) Date of Patent: *Mar. 4, 2025

(54) DIGITAL STETHOSCOPE

(71) Applicant: AliveCor, Inc., Mountain View, CA (US)

(72) Inventors: David Nalin Kumar, San Jose, CA (US); Vinod Khosla, Mountain View, CA (US)

(73) Assignee: ALIVECOR, INC., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/407,322

(22) Filed: Jan. 8, 2024

(65) Prior Publication Data

US 2024/0147150 A1    May 2, 2024

Related U.S. Application Data

(63) Continuation of application No. 17/370,365, filed on Jul. 8, 2021, now Pat. No. 11,882,402.

(51) Int. Cl.
| | |
|---|---|
| *H04R 1/46* | (2006.01) |
| *A61B 7/02* | (2006.01) |
| *A61B 7/04* | (2006.01) |
| *G06F 3/14* | (2006.01) |
| *G10L 25/66* | (2013.01) |
| *G16H 50/20* | (2018.01) |
| *H04R 1/04* | (2006.01) |
| *H04R 1/40* | (2006.01) |
| *H04R 3/00* | (2006.01) |
| *H04R 19/04* | (2006.01) |

(52) U.S. Cl.
CPC ............... *H04R 1/46* (2013.01); *A61B 7/026* (2013.01); *A61B 7/04* (2013.01); *G06F 3/14* (2013.01); *G10L 25/66* (2013.01); *G16H 50/20* (2018.01); *H04R 1/04* (2013.01); *H04R 1/406* (2013.01); *H04R 3/005* (2013.01); *H04R 19/04* (2013.01); *A61B 2562/028* (2013.01); *H04R 2201/003* (2013.01); *H04R 2201/401* (2013.01)

(58) Field of Classification Search
CPC . H04R 1/04; H04R 1/46; H04R 1/406; H04R 3/005; H04R 19/04; H04R 2201/003; H04R 2201/401; G16H 50/20; G06F 3/14; G10L 25/66; A61B 7/026; A61B 7/04; A61B 2562/028
USPC ...................... 381/56, 58, 67, 122, 124, 150
See application file for complete search history.

(56) References Cited

U.S. PATENT DOCUMENTS

| | | | |
|---|---|---|---|
| 2006/0098825 A1* | 5/2006 | Katz ........................ | A61B 7/04 600/528 |
| 2009/0157308 A1* | 6/2009 | Ogawa ............... | G01C 21/3655 701/533 |
| 2011/0087135 A1* | 4/2011 | Ferzli ................... | A61B 5/0035 706/54 |

(Continued)

*Primary Examiner* — William A Jerez Lora (57) ABSTRACT

A digital stethoscope includes a stethoscope housing defining a housing edge. The digital stethoscope also includes a surface region secured to the stethoscope housing at the housing edge, and a number of microphones. The digital stethoscope also includes a processing device disposed within the stethoscope housing and in communication with the microphones. The processing device receives the digital audio data from the microphones.

20 Claims, 7 Drawing Sheets

(56) References Cited

U.S. PATENT DOCUMENTS

| | | | |
|---|---|---|---|
| 2011/0096936 A1* | 4/2011 | Gass | A61B 7/04 381/67 |
| 2011/0222697 A1* | 9/2011 | Dong | A61B 7/026 381/67 |

* cited by examiner

DIGITAL STETHOSCOPE

CROSS-REFERENCE TO RELATED APPLICATIONS

This application is a continuation of U.S. application Ser. No. 17/370,365, filed Jul. 8, 2021 and entitled "DIGITAL STETHOSCOPE," the contents of which are hereby incorporated by reference.

FIELD OF INVENTION

This invention relates generally to a digital stethoscope, and more particularly to systems and methods for detecting and processing digital audio signals using a digital stethoscope.

BACKGROUND OF THE INVENTION

Traditional stethoscopes are acoustic medical devices used for listening to internal sounds within the body. A medical professional can use a traditional acoustic stethoscope to amplify the sounds made by the heart, lungs, or other body parts. A trained professional can detect abnormalities or problems within the body based on these sounds, and significant data exists regarding what types of sounds indicate abnormalities, such as heart murmurs.

SUMMARY OF THE DESCRIPTION

A digital stethoscope, as well as a digital stethoscope system and methods for operating a digital stethoscope are disclosed herein. In an exemplary embodiment, the present disclosure relates to a digital stethoscope including a stethoscope housing defining a housing edge; a surface region secured to the stethoscope housing at the housing edge and capable of being held against the body; microphones; and a processing device disposed within the stethoscope housing and in communication with the microphones to receive digital audio data received by the microphones. In one embodiment, the microphones are disposed symmetrically about the surface region. In one embodiment, the microphones are disposed on an external surface of the surface region. In one embodiment, the microphones are disposed on an internal surface of the surface region. In one embodiment, the digital stethoscope includes an air tube with a coupler to releasably couple with a portion of the stethoscope housing. In one embodiment, the digital stethoscope also functions as an analog stethoscope when the air tube is coupled to the stethoscope housing. In one embodiment, the microphones are micro electro-mechanical system (MEMS) microphones. In one embodiment, the digital stethoscope also includes a communication device within the stethoscope housing and in communication with the processing device to transmit data corresponding to the digital audio data received by the plurality of microphones.

According to another aspect, the present disclosure relates to a digital stethoscope system. The system includes a housing defining a housing edge; a surface region secured to the stethoscope housing at the housing edge and capable of being held against the body; microphones disposed symmetrically on the surface region; and an air tube coupled with a portion of the stethoscope housing at a first end, and terminating in a headset at a second end. The system also includes a processing device in communication with the plurality of microphones to receive digital audio data received by the plurality of microphones. The system also includes a communication device in communication with the processing device; a portable electronic device in communication with the communication device to receive data from the processing device; and a visual display of the portable electronic device. In one embodiment, the processing device determines a location of the housing with respect to an audio source, and the visual display presents a visual representation of the housing with respect to the audio source. In one embodiment, the processing device classifies the digital audio data received by the plurality of microphones. In one embodiment, the processing device is in communication with an artificial intelligence (AI) engine and a database of digital audio data, and the processing device utilizes the AI engine and the database of digital audio data to classify the digital audio data received by the plurality of microphones. In one embodiment, the processing device classifies the digital audio data received by the microphones as coming from a human heart, a lung, a joint, or other human portion. In one embodiment, the processing device classifies the digital audio data received by the microphones as healthy or unhealthy.

According to another aspect, the present disclosure relates to a method of detecting digital audio signals using a digital stethoscope. The method includes receiving audio signals by microphones disposed symmetrically on a surface region of a digital stethoscope, and transmitting digital audio data to a processing device from the microphones. The digital audio data represents the audio signals. The method also includes analyzing the digital audio data using the processing device and generating audio classification data associated with the digital audio data; and generating a database including the digital audio data and the audio classification data. In one embodiment, the processing device is located along an air tube of the digital stethoscope. In one embodiment, the processing device is in communication with an artificial intelligence (AI) engine and a database of digital audio data, and the processing device utilizes the AI engine and the database of digital audio data to classify the digital audio data received by the plurality of microphones. In one embodiment, the processing device classifies the digital audio data received by the microphones as coming from a human heart, a lung, a joint, or other human portion. In one embodiment, the processing device classifies the digital audio data received by the microphones as healthy or unhealthy. In one embodiment, the method also includes: determining a location of the digital stethoscope with respect to an audio source; determining an optimal location of the digital stethoscope with respect to the audio source; and if the digital stethoscope is not in the optimal location, communicating with a portable display device to cause a display of the portable display device to display instructions for moving the digital stethoscope toward the optimal location.

According to another aspect, the present disclosure relates to a digital stethoscope that includes a stethoscope housing defining a housing edge, a surface region secured to the stethoscope housing at the housing edge and capable of being held against the body, a number of microphones disposed on the surface region, and a processing device located within the stethoscope housing and in communication with the microphones to receive digital audio data from the microphones.

According to another aspect, the present disclosure relates to a digital stethoscope that includes a stethoscope housing defining a housing edge, a surface region secured to the stethoscope housing at the housing edge; a number of microphones; and a processing device within the stethoscope housing and in communication with the microphones to receive digital audio data from the microphones.

BRIEF DESCRIPTION OF THE DRAWINGS

The present invention is illustrated by way of example and not limitation in the figures of the accompanying drawings in which like references indicate similar elements.

DETAILED DESCRIPTION

A digital stethoscope and a method of operating a digital stethoscope to detect digital audio signals is disclosed. In the following description, numerous specific details are set forth to provide thorough explanation of embodiments of the present invention. It will be apparent, however, to one skilled in the art, that embodiments of the present invention may be practiced without some or all of these specific details. In other instances, well-known components, structures, and techniques have not been shown or described in detail in order not to obscure the understanding of this description.

Reference in the specification to "one embodiment" or "an embodiment" means that a particular feature, structure, or characteristic described in connection with the embodiment can be included in at least one embodiment of the invention. The appearances of the phrase "in one embodiment" in various places in the specification do not necessarily all refer to the same embodiment.

The methods depicted in the figures and described in the following description, may be performed by processing logic that comprises hardware (e.g., circuitry, dedicated logic, etc.), software (such as is run on a general-purpose computer system or a dedicated machine), or a combination of both. Although the processes are described below in terms of some sequential operations, it should be appreciated that some of the operations described may be performed in different order. Moreover, some operations may be performed in parallel rather than sequentially.

According to one embodiment, a digital stethoscope is disclosed that be used for auscultation to listen to internal sounds within the body. The digital stethoscope can include a housing that is similar to a typical chest piece for an acoustic or analog stethoscope. The digital stethoscope includes a number of detection devices that can be pressed against the body in order to detect sounds from within the body and generate digital audio signals. The detection devices can include, for example, micro electro-mechanical system (MEMS) microphones, and these MEMS microphones can be arranged on the housing or within the housing of the digital stethoscope. For example, the MEMS microphones can be arranged on an interface device that can have a surface region capable of being held against the body. In the case of a digital stethoscope that also functions as an analog stethoscope, this interface device can be the stethoscope surface region. In some embodiments, the digital stethoscope can include a number of MEMS microphones that are arranged symmetrically on the stethoscope.

In some embodiments, the digital stethoscope includes one or more diaphragms or surface regions and is able to also function as an analog stethoscope. In such embodiments, the detection devices can be located on the diaphragm of the stethoscope. For example, a number of MEMS microphones can be attached to an internal or an external surface of the diaphragm, and can also be connected to a processing device within the digital stethoscope. Because MEMS microphones have such a small form factor, they can be located on the diaphragm without significantly impacting the effectiveness of the diaphragm when being used as an analog stethoscope.

In some cases, the processing device within the digital stethoscope can be located within the housing (i.e. within the chest piece). In such embodiments, the chest piece can be removably attached to an air tube of the digital stethoscope, using a coupling mechanism. In alternative embodiments, the processing device can be located along the air tube of the digital stethoscope, closer to the head set and ear tips of the stethoscope.

In some embodiments, the processing device can include an engine to receive digital audio data from the detection devices, parse the information, and identify one or more features of the parsed digital audio data. The digital stethoscope can also include a communication device that is in communication with the processing device, in order to transfer data to and/or from other electronic devices. In some embodiments, the digital stethoscope can also include a pair of speakers coupled to the headset ear tips, the detection devices, and/or the processing device and communication device. The speakers can be coupled to the ears of a user in order to listen to sounds within the body, or to hear other information related to those sounds. For example, the user can simply listen to sounds within the body, or can also listen to information related to those sounds generated by the processing device. In one such example, the processing device can parse or classify the sounds by identifying a feature of the human organ being listened to, and the speakers can be used to provide that information to the user.

Figure 1:
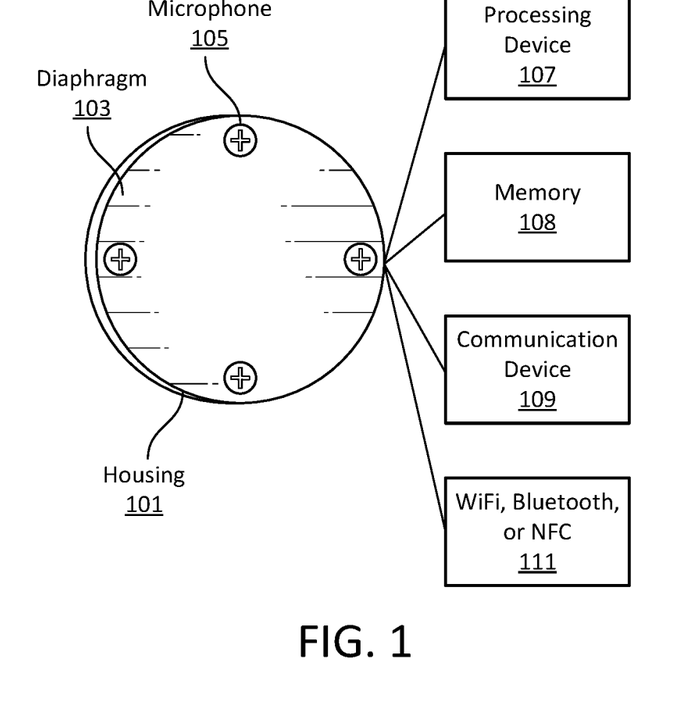
FIG. 1 illustrates a block diagram of an example digital stethoscope, according to an embodiment of the present disclosure.

FIG. 1 illustrates a block diagram of an example digital stethoscope, according to an embodiment of the present disclosure. In this embodiment, the digital stethoscope incudes a housing 101 that defines a housing edge. The housing edge can be circular, like a traditional analog stethoscope, in some embodiments. However, the geometry of the housing is not limited to a circular design. The digital stethoscope also includes a surface region 103 that is secured to the stethoscope housing 101 at the housing edge. The stethoscope also includes a number of microphones 105 disposed on the surface region. In this embodiment, the surface region is circular, and the microphones 105 are disposed symmetrically about surface region near the outer circumference. In the embodiment shown in FIG. 1, four microphones are included, although more or fewer microphones can be utilized in different embodiments, and the microphones do not necessarily need to be located symmetrically about the circumference of the surface region. In alternative embodiments, one or more microphones can be located near the center of the surface region, or arranged across the surface region in a grid, or other pattern. The microphones can include MEMS microphones, in some embodiments.

The digital stethoscope can also include a processing device 107, a communication device 109, and a mobile platform such as WiFi, Bluetooth, or NFC 111. The processing device 107 can be in communication with the microphones 105 and can be used, for example, to analyze digital audio signals. In some embodiments, the processing device 107 can analyze the digital audio signals from the microphones 105 in order to parse or classify the audio signals into different classifications. For example, the processing device 107 can determine whether the digital audio data is received from a human heart, a lung, a joint, or other organ or portion of the body. In some cases, the digital audio data can include data from both the heart and a lung, or some other combination of body parts, and the processing device 107 can parse the different audio signals and distinguish between them.

In some embodiments, the processing device 107 can detect features within the digital audio data and classify the digital audio data accordingly. For example, the processing device 107 may be able to detect the sound of a heart murmur, or a problem with the lungs or abdomen, and can classify the detected audio data accordingly. This classification can also be provided to the user. In some cases, the user can be a doctor or healthcare worker in a more typical care setting. In other cases, the user can be a patient operating the digital stethoscope in a remote or telemedicine setting.

The communication device 109 and mobile platform can be used to communicate with other electronic devices in order to send and/or receive data. In some embodiments, the classification data generated by the digital stethoscope can be provided to the user for a diagnosis. For example, if a heart murmur is detected, the communication device 109 can transmit this information to an electronic device in order to display a notification to the user. In other embodiments, the classification data can be stored in a database along with the digital audio data in order to generate or compile a database of digital audio signals that are associated with different conditions, organs, or other phenomena.

In some embodiments, the processing device 107 can be located onboard the stethoscope within the housing 101. Alternatively, the processing device 107 can be located within another portion of the digital stethoscope, such as along an air tube. In still other embodiments, the processing device 107 can be remote and simply in wireless communication with the microphones 105. In embodiments where the processing device 107 and communication device 109 are located onboard the digital stethoscope, the entire system may begin by initializing and establishing a communication channel between the device and an electronic device, such as a cell phone, tablet, or other mobile computing device. This other mobile electronic device can have a display screen and may be useful for operating the digital stethoscope and receiving or viewing data related to the patient being treated.

Figure 2:
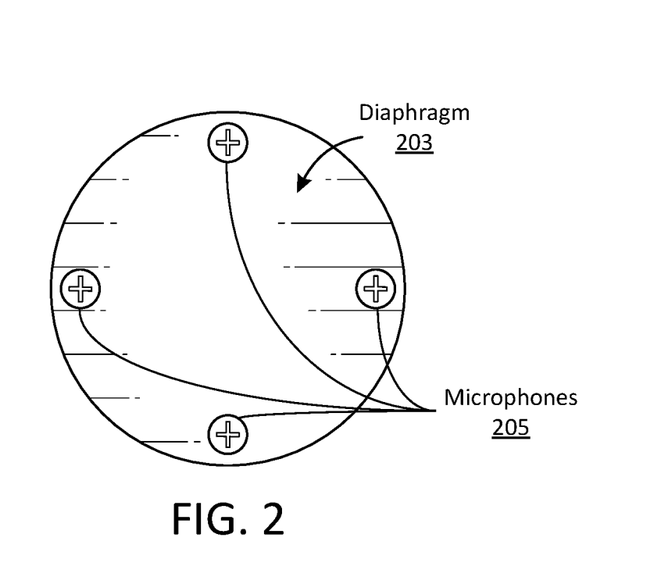
FIG. 2 shows the surface region and microphones of an example digital stethoscope, according to an embodiment of the present disclosure.

FIG. 2 shows the surface region 203 and microphones 205 of an example digital stethoscope, according to an embodiment of the present disclosure. In this embodiment, the surface region 203 that is secured to the stethoscope housing is circular, and includes a number of microphones 205 disposed symmetrically about the surface region near the outer circumference. As with the embodiment shown in FIG. 1, four microphones 205 are shown in FIG. 2. However, more or fewer microphones can be utilized in different embodiments, and the microphones do not necessarily need to be located symmetrically about the circumference of the surface region 203. In alternative embodiments, one or more microphones can be located near the center of the surface region 203, or arranged across the surface region 203 in a grid, or other pattern. The microphones can include MEMS microphones, or other suitable small microphones that can be used to detect sounds within the body.

Figure 3A:
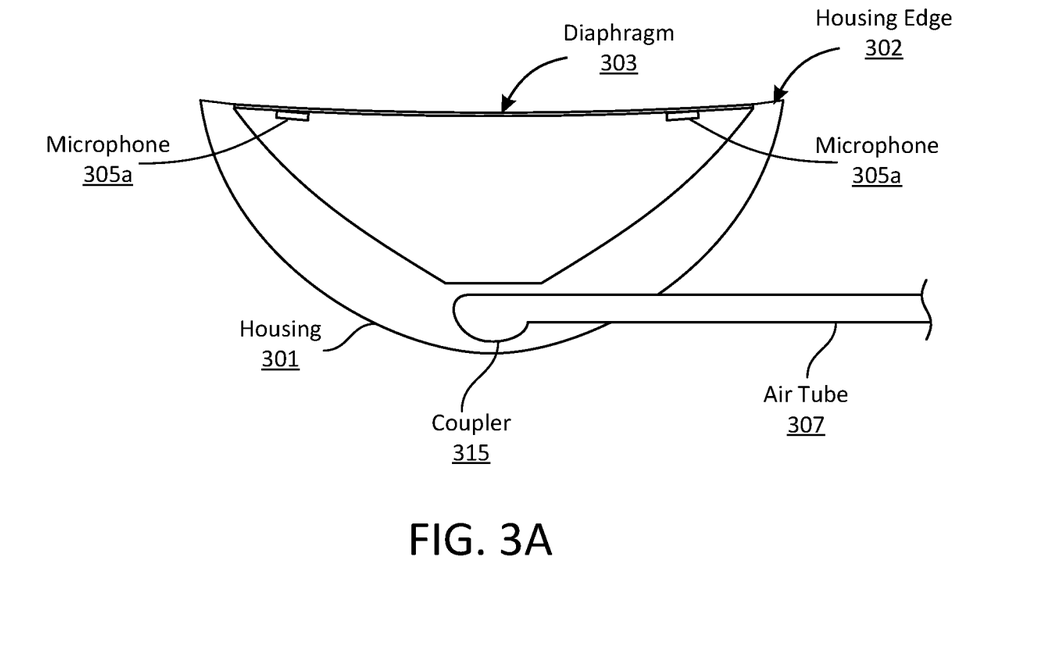
FIG. 3A shows a cross-sectional side view of an example digital stethoscope, according to an embodiment of the present disclosure.

FIG. 3A shows a cross-sectional side view of an example digital stethoscope, according to an embodiment of the present disclosure. In this embodiment, the digital stethoscope includes a housing 301. The housing 301 defines a housing edge 302, that can be circular, as shown in FIGS. 1-2. The surface region 303 can be attached or secured to the housing edge 302 and capable of being held against the body, and the microphones 305a can be attached to or located on the surface region 303. In this particular embodiment, the microphones 305a are shown attached to an internal side of the surface region 303. However, in other embodiments the microphones 305a can be attached to the external surface of the surface region 303. It could also be possible to fabricate the surface region 303 and microphones 305a together such that they are integral with one another, rather than attached or mounted onto one another. In some embodiments the housing 301 may also include a "honeycomb" structure that may provide echo cancelling.

The digital stethoscope of FIG. 3A also includes an air tube 307 that is removably attached to the housing 301 using a coupler 315. In this embodiment, the coupler 315 is designed to mate with or fit within a portion of the housing 301. However, in other embodiments the coupler 315 and housing 301 can be designed such that the coupler 315 attaches to an exterior portion of the housing 301. When the air tube 307 is attached to the housing 301 using the coupler 315, the digital stethoscope can also function as an analog stethoscope.

Figure 3B:
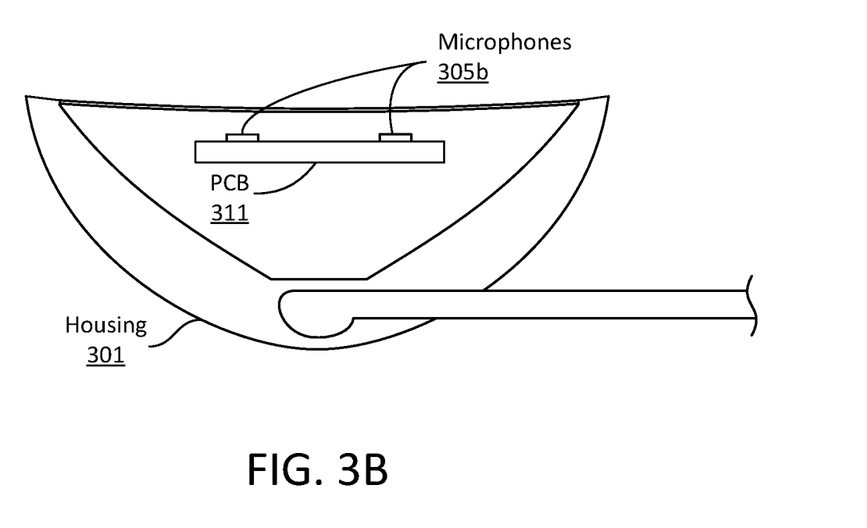
FIG. 3B shows a cross-sectional side view of another example digital stethoscope, according to an embodiment of the present disclosure.

FIG. 3B shows a cross-sectional side view of another example digital stethoscope, according to an embodiment of the present disclosure. In this embodiment, the digital stethoscope is similar to the stethoscope of FIG. 3A, and includes corresponding components, as well as a PCB 311, located within the housing 301. The PCB 311 can be in communication with the microphones 305b, and can receive audio data from the microphones 305b. In some embodiments, the PCB 311 can analyze or process the audio data received from the microphones 305a according to the methods disclosed below. The microphones 305b can be mounted on the PCB 311, or both components can be fabricated as a single piece. In some embodiments, the PCB 311 can be mounted to or secured to the interior portion of the housing 301. For example, the PCB 311 can be secured to the housing 301 using thin posts or other means, such that the PCB 311 is secured in place. The PCB can analyze or process the audio data received from the microphones 305b according to the methods disclosed below.

Figure 4:
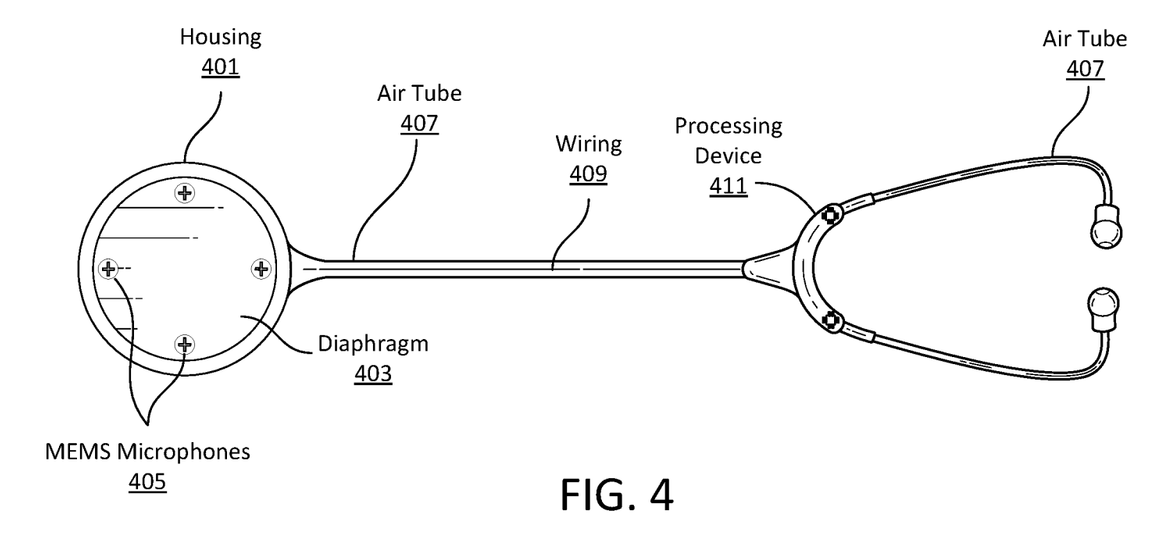
FIG. 4 shows a plan view of an example digital stethoscope with an air tube, according to an embodiment of the present disclosure.

FIG. 4 shows a plan view of an example digital stethoscope with an air tube, according to an embodiment of the present disclosure. In this embodiment, the digital stethoscope includes an air tube 407 connected to the housing 401, and the housing includes a surface region 403 and a number of MEMS microphones 405 such that the digital stethoscope can also function as an analog stethoscope. In some embodiments, the air tube 407 can be removably attached to the housing 401, as discussed above in reference to FIG. 3A. However, this is not necessary and the air tube 407 can be permanently mounted to the housing 401. Because the digital stethoscope includes an air tube with a headset and ear tips, the processing device 411 can be located away from the housing. This can prevent any interference between the processing device 411 and the surface region 403, or simply provide additional flexibility in design and more options for electronic components. The processing device 411 can be in communication with the MEMS microphones 405 via wiring 409. In embodiments where the air tube 407 is removably attached to the housing 401 using a coupler, as discussed in FIG. 3A, the coupler can also include an electronic coupler that can complete the connection between the wiring 409 and the MEMS microphones 405.

Figure 5:
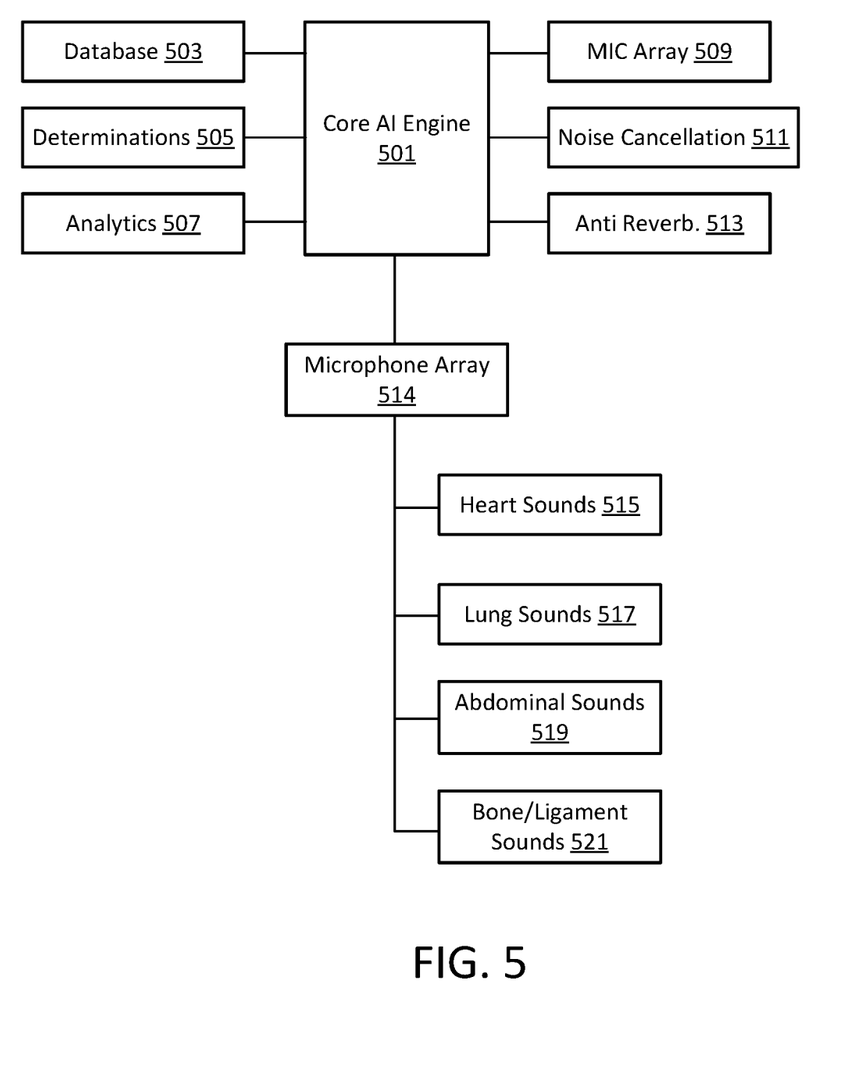
FIG. 5 shows a block diagram of an example digital stethoscope system, according to an embodiment of the present disclosure.

FIG. 5 shows a block diagram of an example digital stethoscope system, according to an embodiment of the present disclosure. In this embodiment, the system includes a core AI engine 501 that can receive inputs from the microphone array 509 on the digital stethoscope. In some embodiments, in order to properly isolate and identify sounds, noise cancellation 511 and anti-reverberation 513 can be performed. The noise cancellation 511 and anti-reverberation 513 may assist in suppressing radio frequency (RF)/electromagnetic noise, physical noise, and noise caused by movement of the digital stethoscope. In some embodiments, one or more of AI engine 501, noise cancellation 511, anti-reverberation 513, and analytics 507 may comprise software or logic that is stored on a processing device located on the digital stethoscope (e.g., processing device 107 illustrated in FIG. 1), or can be stored on a memory of the digital stethoscope (e.g., memory 108 illustrated in FIG. 1), and executed using the processing device located on the digital stethoscope (e.g., processing device 107). In other embodiments, one or more of AI engine 501, noise cancellation 511, anti-reverberation 513, and analytics 507 may comprise dedicated hardware/circuitry or other form of processing core that executes program code instructions.

In some embodiments, the core AI engine 501 can include a machine learning (ML) model that is trained on a set of training data, which may be stored in the database 503. In some embodiments, such a model can be trained using annotated training data, such as digital audio data that is known to correspond to a particular phenomenon or condition, such as a heart murmur or a lung disease. Such a model is considered a supervised ML model. The core AI engine 501 can include, in some embodiments, a feature extractor or other type of unsupervised learning model that can analyze audio data and identify features or other characteristics within the data. One skilled in the art will recognize that a combination of supervised and unsupervised models can be used, and the level at which annotations can be provided to the model can vary depending on the scenario. For example, the annotated training data can include annotations related to specific segments within a digital audio file, or annotations related to specific components of an audio file that have been parsed or classified by the processing device.

Once a ML model has been trained, it can receive inputs from the digital stethoscope via a microphone array 514 in the form of heart sounds 515, lung sounds 517, abdominal sounds 519, and/or bone or ligament sounds 521. These types of sounds are merely examples, and are not intended to be an all-inclusive or complete list of the types of sounds that can be detected or identified using the core AI engine 501. The input sounds may be captured by microphones of the digital stethoscope (e.g., microphones 205 and 305 illustrated in FIGS. 2 and 3 respectively) and digitized by an analog to digital converter (not shown) that may e.g., be part of processor 107. The core AI engine 501 can then implement various analytics 507 and generate determinations 505 about the digital audio data.

The determinations that can be made by the core AI engine 501 include, for example, determinations related to a physical phenomenon, such as heart murmur, acid reflux, etc. The core AI engine 501 can also analyze the digital audio data and identify whether the sound is from a heart, lungs, or other body part. Heart rate, and other attributes related to a body part can also be determined. In some cases, the core AI engine 501 can analyze the digital audio data to determine whether the sounds come from a healthy or unhealthy organ or body part.

The digital stethoscope system can also include a recording device and storage system (as discussed in more detail below), in some embodiments and can be in communication with other electronic devices in order to send and receive information, or transmit notifications. The digital stethoscope system can prompt a mobile electronic device to display certain graphical images or data representing the digital audio data, or representing different determinations or analytics that are performed by the core AI engine 501.

Figure 6:
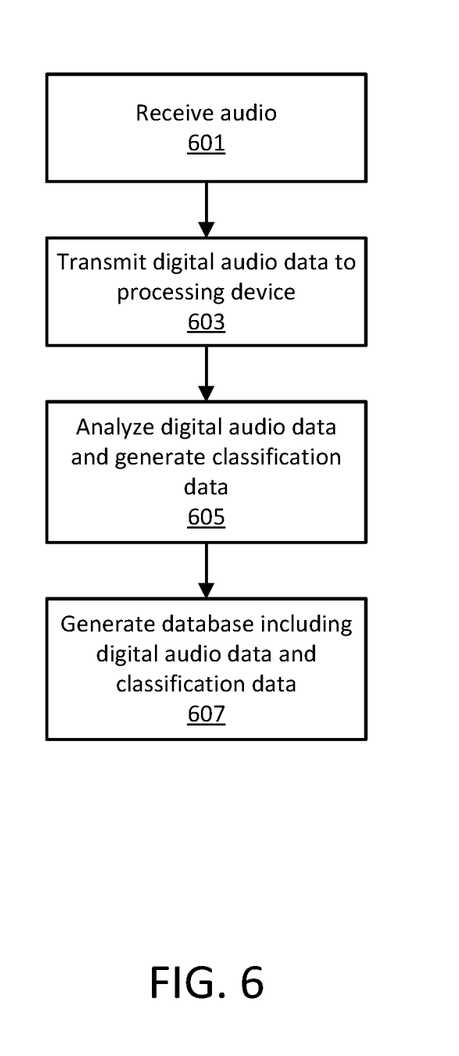
FIG. 6 shows a flow diagram of an example method of detecting digital audio signals using a digital stethoscope, according to an embodiment of the present disclosure.

FIG. 6 shows a flow diagram of an example method of detecting digital audio signals using a digital stethoscope, according to an embodiment of the present disclosure. The method can begin at operation 601 with receiving audio signals at a number of microphones. As discussed above, the microphones can include MEMS microphones that are disposed on a surface region of a digital stethoscope. The audio signals can be the sounds generated by a body part, such as the heart, lungs, abdomen, etc. and the MEMS microphones can generate digital audio data representing the audio signals.

At operation 603, the microphones transmit the digital audio data to a processing device. The processing device can be located nearby the microphones within a device housing, or at another location on the digital stethoscope. In some cases, the processing device includes an AI engine, as discussed above, or is in communication with other electronic devices with access to the AI engine.

At operation 605, the digital audio data is analyzed, and audio classification data is generated associated with the digital audio data. This classification data can include, for example, information identifying the sounds as coming from a particular body part, information indicating the health of the body part being listened to, or other information that can be linked to the digital audio data and the patient. In one embodiment, the processing device is in communication with an AI engine and a database of digital audio data. The processing device can utilize the AI engine and the database of digital audio data to classify the digital audio data received by the microphones.

At operation 607, a database is generated including the digital audio data and the audio classification data. In some embodiments, the database can include copies of the actual digital audio data or audio files, while in other embodiments the digital audio data can include a description of the sounds detected or a link to the actual audio files. As discussed above, the audio classification data can include information indicating the source of the audio (e.g. whether the audio is coming from a human heart, a lung, a joint, or other human portion), the health of the patient, etc.

Figure 7:
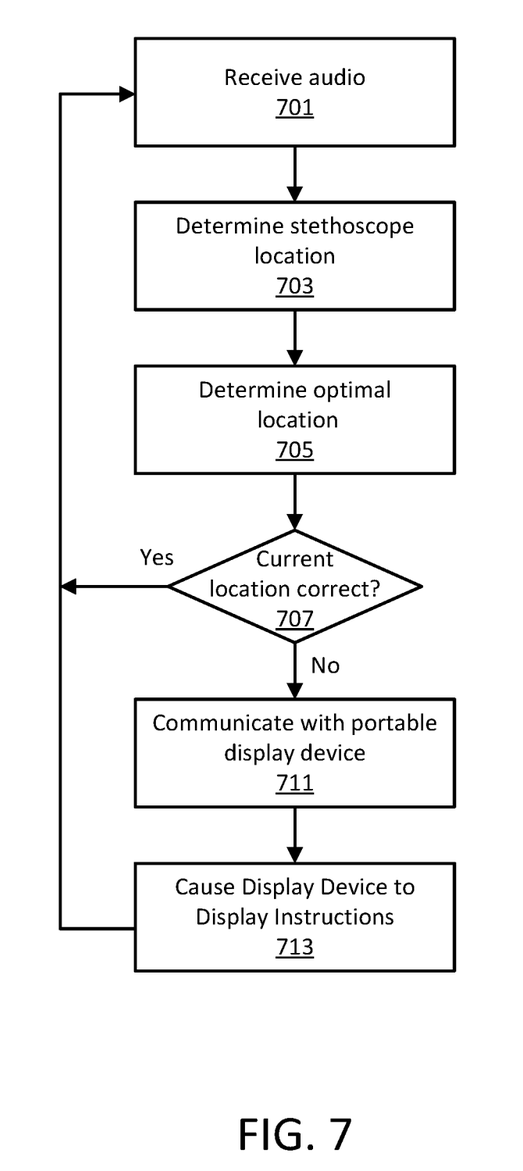
FIG. 7 shows a flow diagram of an example method of operating a digital stethoscope, according to an embodiment of the present disclosure.

FIG. 7 shows a flow diagram of an example method of operating a digital stethoscope, according to an embodiment of the present disclosure. The method can begin at operation 701 with receiving audio signals at a number of microphones. As discussed above, the microphones can include MEMS disposed on a surface region of a digital stethoscope. The audio signals can be the sounds generated by a body part, such as the heart, lungs, abdomen, etc. and the MEMS microphones can generate digital audio data representing the audio signals. The MEMS microphones can be dispersed around the surface region in a known orientation, such that beamforming can be performed.

At operation 703, the processing device can determine the location of the digital stethoscope—or more specifically the location of the MEMS microphones—with respect to the audio source. For example, if the digital stethoscope is being used to listen to a heartbeat, the processing device can analyze the digital audio signals from the microphones and determine the location of the stethoscope with respect to the heart.

At operation 705, the processing device can determine the optimal location of the digital stethoscope with respect to the audio source. Returning to the example of listening to a heartbeat, the processing device knows the location of the stethoscope with respect to the heart and can determine the optimal location for listening to a heartbeat. In other embodiments, different organs or body parts can be the target of interest, and there can be different optimal locations of the stethoscope depending on the audio data that is intended to be gathered.

Once the location of the digital stethoscope is determined, as well as the optimal location of the stethoscope, the method can continue at operation 707 with determining if the stethoscope is currently in the correct location. If so, the method can return to operation 701 and continue receiving audio data at the microphones.

If the stethoscope is not at the optimal location, the method can continue at operation 711 and communicate with a portable display device. At operation 713, the digital stethoscope causes the display of the portable display device to display instructions for moving the digital stethoscope toward the optimal location. Such instructions can be particularly helpful in the telemedicine or remote treatment settings, where a patient may need to operate the digital stethoscope without the guidance of a trained medial professional.

Figure 8:
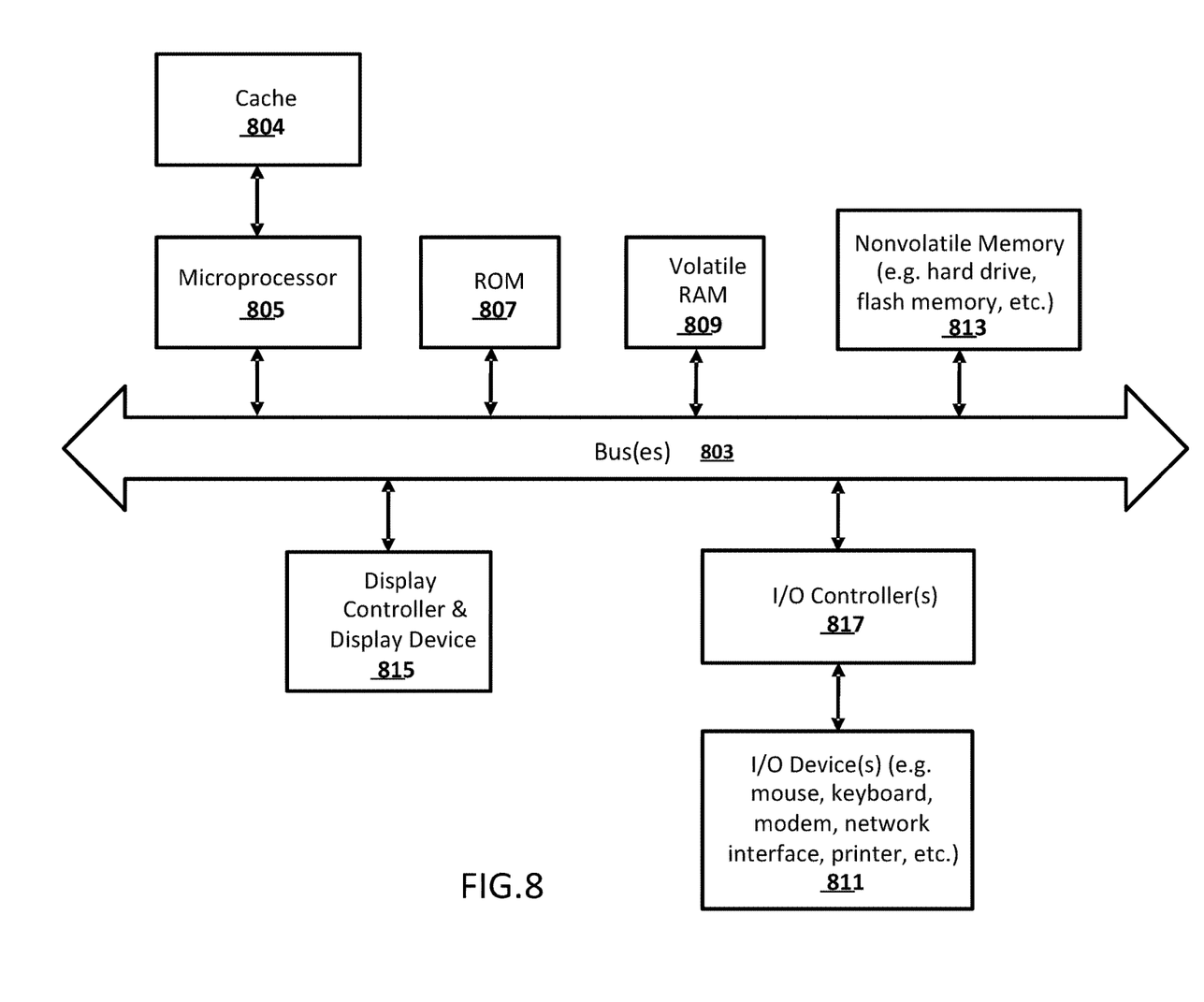
FIG. 8 illustrates an example computer system which may be used in conjunction with the embodiments described herein.

FIG. 8 illustrates an example computer system which may be used in conjunction with the embodiments described herein. As shown in FIG. 8, the computer system, which is a form of a data processing system, includes a bus 803 which is coupled to a microprocessor(s) 805 and a ROM (Read Only Memory) 807 and volatile RAM (Random Access Memory) 809 and a non-volatile memory 813. The microprocessor 805 may include one or more CPU(s), GPU(s), a specialized processor, and/or a combination thereof. The microprocessor 805 may be in communication with a cache 804, and may retrieve the instructions from the memories 807, 809, 813 and execute the instructions to perform operations described above. The bus 803 interconnects these various components together and also interconnects these components 805, 807, 809, and 813 to a display controller and display device 815 and to peripheral devices such as input/output (I/O) devices 811 which may be mice, keyboards, modems, network interfaces, printers and other devices which are well known in the art. Typically, the input/output devices 811 are coupled to the system through input/output controllers 817. The volatile RAM 809 is typically implemented as dynamic RAM (DRAM), which requires power continually in order to refresh or maintain the data in the memory.

The nonvolatile memory 813 can be, for example, a magnetic hard drive or a magnetic optical drive or an optical drive or a DVD RAM or a flash memory or other types of memory systems, which maintain data (e.g. large amounts of data) even after power is removed from the system. Typically, the nonvolatile memory 813 will also be a random access memory although this is not required. While FIG. 8 shows that the nonvolatile memory 813 is a local device coupled directly to the rest of the components in the data processing system, it will be appreciated that the present invention may utilize a nonvolatile memory which is remote from the system, such as a network storage device which is coupled to the data processing system through a network interface such as a modem, an Ethernet interface or a wireless network. The bus 803 may include one or more buses connected to each other through various bridges, controllers and/or adapters as is well known in the art.

Portions of what was described above may be implemented with logic circuitry such as a dedicated logic circuit or with a microcontroller or other form of processing core that executes program code instructions. The microcontroller or processing core may be located onboard the digital stethoscope, or on an electronic device or remote server that is in communication with the digital stethoscope. Processes taught by the discussion above may be performed with program code, such as machine-executable instructions, that cause a machine that executes these instructions to perform certain functions. In this context, a "machine" may be a machine that converts intermediate form (or "abstract") instructions into processor specific instructions (e.g., an abstract execution environment such as a "virtual machine" (e.g., a Java Virtual Machine), an interpreter, a Common Language Runtime, a high-level language virtual machine, etc.), and/or, electronic circuitry disposed on a semiconductor chip (e.g., "logic circuitry" implemented with transistors) designed to execute instructions such as a general-purpose processor and/or a special-purpose processor. Processes taught by the discussion above may also be performed by (in the alternative to a machine or in combination with a machine) electronic circuitry designed to perform the processes (or a portion thereof) without the execution of program code.

The present invention also relates to an apparatus for performing the operations described herein. This apparatus may be specially constructed for the required purpose, or it may comprise a general-purpose computer selectively activated or reconfigured by a computer program stored in the computer. Such a computer program may be stored in a computer readable storage medium onboard the digital stethoscope, or on a device that is in communication with the digital stethoscope.

A machine readable medium includes any mechanism for storing or transmitting information in a form readable by a machine (e.g., a computer). For example, a machine readable medium includes read only memory ("ROM"); random access memory ("RAM"); magnetic disk storage media; optical storage media; flash memory devices; etc.

An article of manufacture may be used to store program code. An article of manufacture that stores program code may be embodied as, but is not limited to, one or more memories (e.g., one or more flash memories, random access memories (static, dynamic or other)), optical disks, CD-ROMs, DVD ROMs, EPROMs, EEPROMs, magnetic or optical cards or other type of machine-readable media suitable for storing electronic instructions. Program code may also be downloaded from a remote computer (e.g., a server) to a requesting computer (e.g., a client) by way of data signals embodied in a propagation medium (e.g., via a communication link (e.g., a network connection)).

In addition, while reference may be made herein to quantitative measures, values, geometric relationships or the like, unless otherwise stated, any one or more if not all of these may be absolute or approximate to account for acceptable variations that may occur, such as those due to manufacturing or engineering tolerances or the like.

The foregoing discussion merely describes some exemplary embodiments of the present invention. One skilled in the art will readily recognize from such discussion, the accompanying drawings, and the claims that various modifications can be made without departing from the spirit and scope of the invention.

What is claimed is:

1. A system, comprising:
    a digital stethoscope comprising:
        a stethoscope housing; and
        a plurality of microphones secured to a surface region of the stethoscope housing, wherein the stethoscope housing defines a circular housing edge; and
    a mobile computing device communicatively coupled to the digital stethoscope, the mobile computing device to:
        receive digital audio data from the plurality of microphones;
        analyze the digital audio data to determine a location of the digital stethoscope;
        determine an optimal location of the digital stethoscope;
        if the digital stethoscope is not in the optimal location, generate instructions for moving the digital stethoscope toward the optimal location; and
        display the instructions for moving the digital stethoscope toward the optimal location.

2. The system of claim 1, wherein the mobile computing device is further to:
    analyze the digital audio data to generate audio classification data associated with the digital audio data; and
    classify, based on the audio classification data, the digital audio data as being received from an audio source.

3. The system of claim 2, wherein the audio source comprises one of a heart, a lung, a joint, an abdomen or other body part.

4. The system of claim 2, wherein the mobile computing device determines the location of the digital stethoscope with respect to the audio source and determines the optimal location of the digital stethoscope with respect to the audio source.

5. The system of claim 2, wherein the mobile computing device is further to:
    generate a database including the digital audio data and the audio classification data.

6. The system of claim 2, wherein the mobile computing device displays a visual representation of the location of the stethoscope housing with respect to the audio source.

7. The system of claim 1, wherein the mobile computing device displays graphical images representing the digital audio data.

8. The system of claim 1, wherein the mobile computing device is further to:
    classify the digital audio data as indicative of an abnormality; and
    transmit the classification to the portable electronic device.

9. The system of claim 8, wherein the mobile computing device displays the classification.

10. The system of claim 2, wherein the mobile computing device uses an artificial intelligence (AI) engine to classify the digital audio data as being received from an audio source.

11. A method comprising:
    receiving audio signals by a plurality of microphones of a digital stethoscope, the plurality of microphones secured to a surface region of a stethoscope housing of the digital stethoscope, the stethoscope housing defining a circular housing edge;
    transmitting, by the plurality of microphones, digital audio data representing the audio signals to a mobile computing device;
    analyzing, by the mobile computing device, the digital audio data to determine a location of the digital stethoscope;
    determining an optimal location of the digital stethoscope;
    if the digital stethoscope is not in the optimal location, generating instructions for moving the digital stethoscope toward the optimal location; and
    displaying, on a display of the portable electronic device, the instructions for moving the digital stethoscope toward the optimal location.

12. The method of claim 11, further comprising:
    analyzing the digital audio data to generate audio classification data associated with the digital audio data; and
    classifying, based on the audio classification data, the digital audio data as being received from an audio source.

13. The method of claim 12, wherein the audio source comprises one of a heart, a lung, a joint, an abdomen or other body part.

14. The method of claim 12, wherein the location of the digital stethoscope is determined with respect to the audio source and the optimal location of the digital stethoscope is determined with respect to the audio source.

15. The method of claim 12, further comprising:
    generating a database including the digital audio data and the audio classification data.

16. The method of claim 12, further comprising:
    displaying, on the display of the mobile computing device, a visual representation of the location of the digital stethoscope with respect to the audio source.

17. The method of claim 11, further comprising:
    displaying, on the display of the portable electronic device, graphical images representing the digital audio data.

18. The method of claim 11, further comprising:
    classifying the digital audio data as indicative of an abnormality; and
    transmitting the classification to the portable electronic device.

19. The method of claim 18, further comprising:
    displaying the classification on the portable electronic device.

20. The method of claim 12, wherein the digital audio data is classified as being received from an audio source using an artificial intelligence (AI) engine.

* * * * *